(12) United States Patent  
Kenyon

(10) Patent No.: US 9,068,915 B2  
(45) Date of Patent: Jun. 30, 2015

(54) METHOD AND SYSTEM FOR CALIBRATING A FLOW CYTOMETER

(71) Applicant: OJK Consulting Ltd, Middlesex (GB)

(72) Inventor: Oliver Kenyon, Middlesex (GB)

(73) Assignee: OJK Consulting Ltd., Northwood, Middlesex (GB)

( * ) Notice: Subject to any disclaimer, the term of this patent is extended or adjusted under 35 U.S.C. 154(b) by 76 days.

(21) Appl. No.: 13/779,701

(22) Filed: Feb. 27, 2013

(65) Prior Publication Data

US 2013/0242296 A1    Sep. 19, 2013

(30) Foreign Application Priority Data

Feb. 28, 2012  (GB) .................................. 1203422.9

(51) Int. Cl.
| | | |
|---|---|---|
| *G01N 15/14* | (2006.01) | |
| *G01N 31/00* | (2006.01) | |
| *G01N 15/10* | (2006.01) | |

(52) U.S. Cl.
CPC ........ *G01N 15/1459* (2013.01); *G01N 15/1012* (2013.01); *G01N 2015/1018* (2013.01)

(58) Field of Classification Search
CPC .............. G01N 15/14; G01N 15/1012; G01N 15/1459; G01N 2015/1018
USPC ........... 356/335–343, 243.1, 243.2; 435/7.21, 435/967; 436/8, 10, 800, 63, 164, 166; 377/29, 12
See application file for complete search history.

(56) References Cited

U.S. PATENT DOCUMENTS

| 5,084,394 | A | | 1/1992 | Vogt et al. |
| 5,540,494 | A | | 7/1996 | Purvis et al. |
| 5,837,547 | A | * | 11/1998 | Schwartz ........................ 436/10 |
| 6,074,879 | A | * | 6/2000 | Zelmanovic et al. ........... 436/10 |
| 7,800,754 | B2 | * | 9/2010 | Kenyon ........................ 356/337 |
| 2009/0071225 | A1 | * | 3/2009 | Schilffarth ..................... 73/1.02 |

FOREIGN PATENT DOCUMENTS

| EP | 257759 | 3/1988 |
| EP | 887637 | 12/1998 |

OTHER PUBLICATIONS

Search Report for GB1203422.9 mailed by the Intellectual Property Office on May 11, 2012 (3 pages).

* cited by examiner

*Primary Examiner* — Hoa Pham  
(74) *Attorney, Agent, or Firm* — Arent Fox LLP

(57) ABSTRACT

A method and system for calibrating a flow cytometer to a refractive index X, the method comprising: analyzing a first mixture of particles in the cytometer and recording the results produced, wherein the first mixture comprises particles having refractive index X, wherein the particles of refractive index X have a plurality of different sizes; analyzing a second mixture of particles in the cytometer and recording the results produced, wherein the second mixture comprises particles having refractive index Y, wherein refractive index Y does not equal refractive index X, and wherein the particles of refractive index Y have a plurality of different sizes, wherein there is at least a partial overlap between the particle sizes in the first and second mixtures, and wherein the size of at least one particle of the second mixture is known; and using the results produced by the first and second mixture to calibrate the cytometer to refractive index X.

20 Claims, 4 Drawing Sheets

METHOD AND SYSTEM FOR CALIBRATING A FLOW CYTOMETER

This application claims priority to British Application No. 1203422.9, entitled "METHOD AND SYSTEM FOR CALIBRATING A FLOW CYTOMETER" filed Feb. 28, 2012, the entirety of which is incorporated herein by reference.

This invention relates to a method and system for calibrating the particle measuring and counting apparatus, as incorporated into flow cytometers.

A flow cytometer counts, measures and discriminates particles in a liquid by their optical properties as they flow through a beam of illuminating radiation one particle at a time. The radiation source is typically a laser and the machine is normally used to count and identify particles at rates up to roughly 100000 particles per second.

The sample is normally prepared by labeling it with one or more fluorescent markers. Each fluorescent marker emits light of a characteristic wavelength range (colour) when it is excited by the laser light. The fluorescent marker may be present in the particle in a quantity roughly proportional to a substance in the particle (for example the particle's DNA content), and therefore the fluorescence signals may indicate certain features of the particle.

Flow cytometers are typically equipped with several optical detectors. Independent optical detectors may be fitted to measure light scattered at a variety of angle ranges, typically described as Small Angle Light Scatter (roughly 1 to 15 degrees, "SALS"), Medium Angle Light Scatter (roughly 15 to 60 degrees, "MALS") and Large Angle Light Scatter (typically greater than 60 degrees, "LALS"), and optical detectors to measure several different colours of fluorescence. The scatter angles are chosen to optimise the resolution between different populations of particle.

The sample liquid is hydro-dynamically focused into a narrow sample core. This may be done by a sheath fluid as it flows into the flow cell channel. Particles in the sample liquid thus pass through a point of detection in the flow cell channel one at a time and are measured individually. A light source (typically a laser) is focused at the point of detection in the flow channel and this light is scattered by particles travelling through the flow cell. If labeled with a fluorescent marker, the particles will also emit light by fluorescence.

The scattered and fluoresced light is converted to an electrical pulse by optical detectors (typically photomultipliers), and the size and shape of these pulses is recorded by computer. The pulse measurements are typically plotted on histogram graphs such that particles with different characteristics form distinct populations on the histograms.

Flow cytometers therefore do not provide absolute particle data. Instead they give signals from light scattered by the particles, where these signals are a function of particle size, shape, structure and refractive index. In order to relate the signals to particle size, flow cytometers are typically calibrated using plastic beads, usually polystyrene beads, of known size, shape and refractive index.

Flow cytometers are therefore typically calibrated by producing a liquid suspension of the plastic beads, hydro-dynamically focusing this liquid suspension into a narrow sample core that allows the plastic beads to pass through a point of detection in the flow cell channel one at a time, and focusing a light source at the point of detection in the flow channel. The light is scattered by the plastic beads travelling through the flow cell, and these light signals are used to calibrate the flow cytometer's scattered light signals to particle size.

Polystyrene beads have a refractive index of approximately 1.59. If the particles to be measured in the cytometer have a refractive index that does not match that of the polystyrene beads, calibrating the cytometer using the polystyrene beads can give an unreliable estimate of the particle size.

For example, biological particles such as bacteria or cell derived microparticles typically have a refractive index less than 1.59, usually in the range 1.33 to 1.50, the exact refractive index of a biological particle being dependent on its composition, for example the relative lipid content versus water content. Therefore calibrating a cytometer with polystyrene beads before using it to analyse a biological sample often gives an unreliable estimate of the biological particle size.

The refractive index of the polystyrene beads and biological particles can be measured using a refractometer.

It is not practical just to calibrate the cytometer using reference particles that have a refractive index that matches that of the particles to be studied in the cytometer, for example the biological particles. This is because it is very difficult to find stable particles that are of precisely known size and have the correct refractive index.

The present invention therefore provides an improved method and system for calibrating a flow cytometer before the cytometer is used to analyse a sample. The sample analysed by the cytometer can comprise, for example, cell derived microvesicles or microparticles, microspheres, cells such as blood cells, parts of cells such as nuclei, bacteria, viruses, or eukaryotic cells.

According to the present invention there is a method of calibrating a flow cytometer to a refractive index X, the method comprising:
  analysing a first mixture of particles in the cytometer and recording the results produced, wherein the first mixture comprises particles having refractive index X, wherein the particles of refractive index X have a plurality of different sizes;
  analysing a second mixture of particles in the cytometer and recording the results produced, wherein the second mixture comprises particles having refractive index Y, wherein refractive index Y does not equal refractive index X, and wherein the particles of refractive index Y have a plurality of different sizes, wherein there is at least a partial overlap between the particle sizes in the first and second mixtures, and wherein the size of at least one particle of the second mixture is known; and
  using the results produced by the first and second mixture to calibrate the cytometer to refractive index X.

Preferably, the second mixture comprises particles of refractive index Y that have at least a plurality of known discrete sizes.

The particles of the second mixture having known discrete sizes are preferably beads of plastic, latex, silica or any other suitable material.

At least some of the particles of the first and second mixtures with refractive indexes X and Y may comprise one or more fluorescence molecules, wherein the relationship between the fluorescence of particles of the first and second mixtures is known.

Preferably, the first mixture comprises an emulsion and particles of the first mixture comprise droplets of a liquid of the emulsion with refractive index X.

Preferably, the second mixture comprises an emulsion and the particles of the second mixture comprise droplets of a liquid of the emulsion with refractive index Y.

Preferably, the droplets are formed from oils, and the emulsions preferably also comprise water (i.e. the first and second mixtures preferably comprise "oil-in-water emulsions").

The size of the particles in the first and second mixtures preferably lies in a range between 50 nm and 50 µm.

The refractive index X preferably lies in the range 1.34 to 1.58.

The results may be recorded from the first or second mixtures independently. Alternatively, the results may be recorded from the first and second mixtures simultaneously.

Preferably, the method further comprises:
using the results produced by the first mixture of particles to produce a first plot on a flow cytometer histogram;
using the results produced by the second mixture of particles to produce a second plot on a flow cytometer histogram;
recording where the plurality of known particle sizes of the second mixture lie on the second plot; and
using the position of the known particle sizes on the second plot to determine where the particles of the same size lie on the first plot.

The flow cytometer histograms may be one-dimensional histograms of a count of the number of particles versus the strength of the signal produced by the particle in the flow cytometer.

Alternatively, the flow cytometer histograms are two-dimensional histograms of two light scatter angle ranges with a count of the number of particles as a density gradient. The flow cytometer histograms may be two-dimensional histograms of the small-angle scatter versus the large-angle scatter.

Alternatively, the flow cytometer histograms may be two-dimensional histograms of a light scatter signal and a fluorescence signal with a count of the number of particles as a density gradient.

According to the present invention there is also a system for calibrating a flow cytometer to a refractive index X, the system comprising:
a first mixture of particles, wherein the first mixture comprises particles of refractive index X, wherein the particles of refractive index X have a plurality of different sizes; and
a second mixture of particles, wherein the second mixture comprises particles of refractive index Y, wherein refractive index Y does not equal refractive index X, and wherein the particles of refractive index Y have a plurality of different sizes, wherein there is at least a partial overlap between the particle sizes in the first and second mixtures, and wherein the size of at least one particle of the second mixture is known.

Embodiments of the invention will now be described, by way of example only, with reference to the accompanying drawings, in which.

Figure 1:
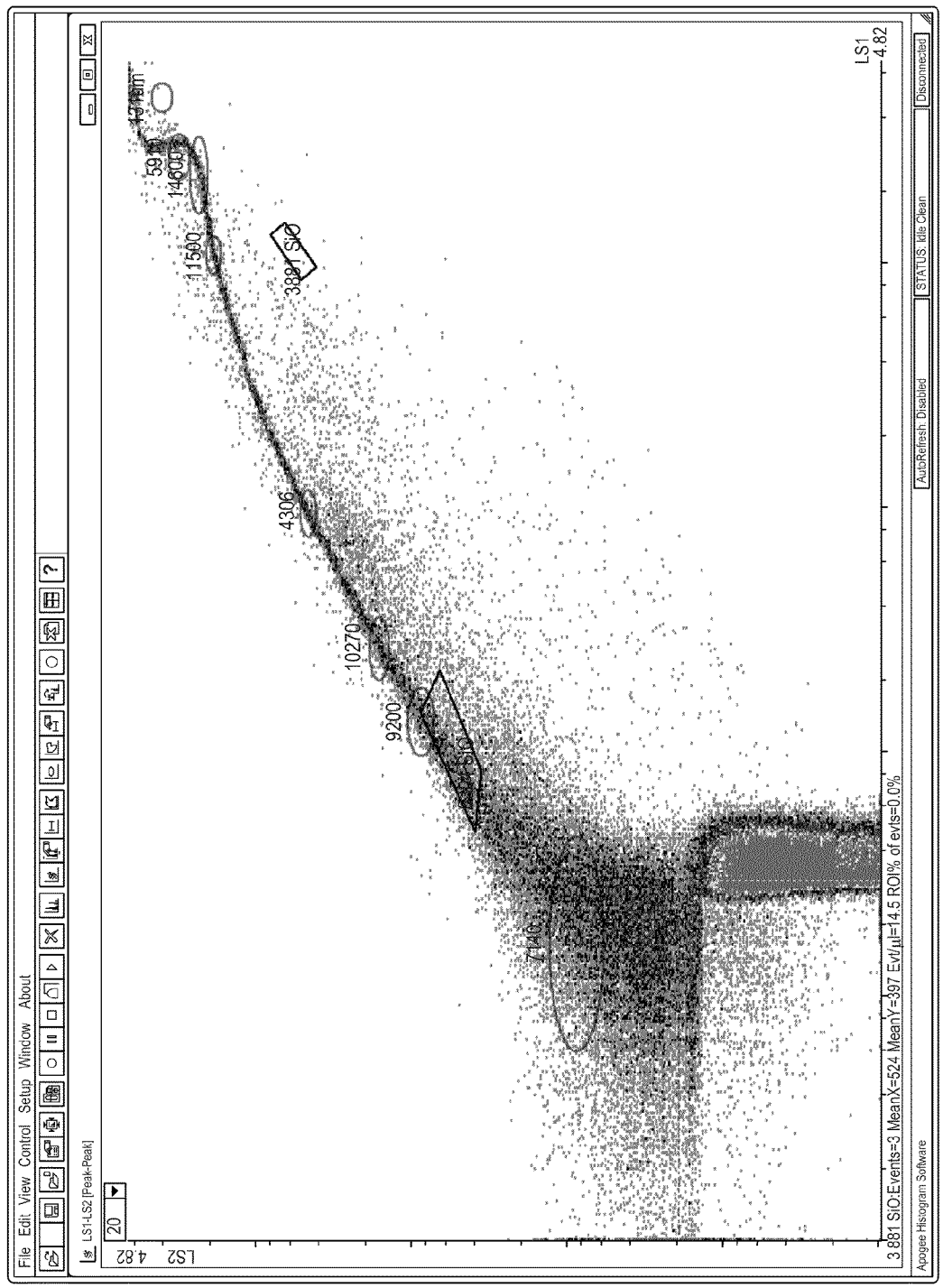
FIG. 1 shows a flow cytometer histogram produced by an oil-in-water emulsion where the oil has a refractive index of 1.59.
Figure 2:
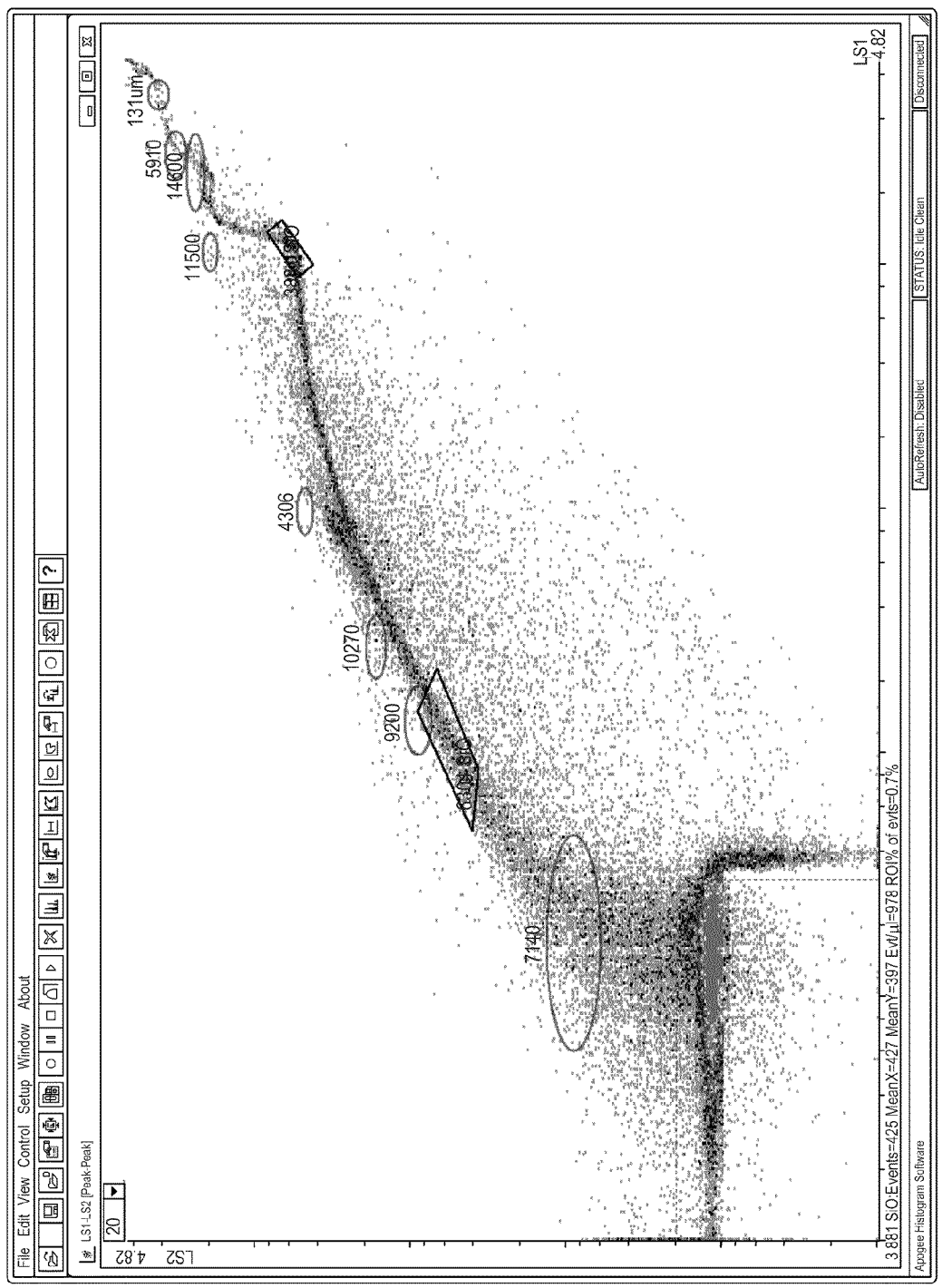
FIG. 2 shows a flow cytometer histogram produced by an oil-in-water emulsion where the oil has a refractive index of 1.42.
Figure 3:
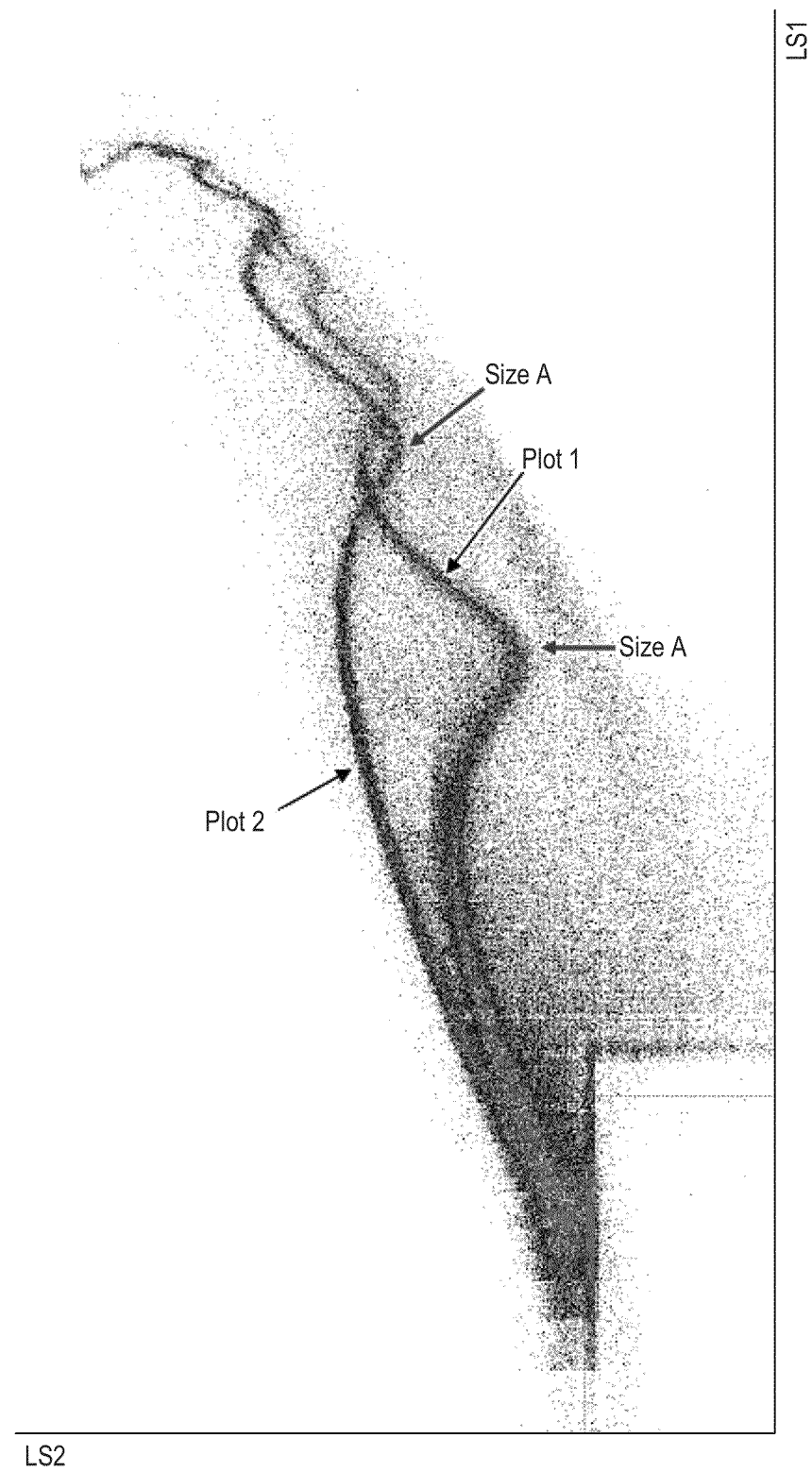
FIG. 3 shows a flow cytometer histogram produced by two different oil-in-water emulsions, the oil of one emulsion having a refractive index of 1.515, and the oil of the other emulsion having a refractive index of 1.404.

Referring to FIGS. 1 to 3, it is well known in the art that, when an oil is purchased from a manufacturer, the refractive indexes of the oil used is specified by the manufacturer, for example on the packaging of the oil (such as on the bottle), or on associated information supplied with the oil.

Oils that are suitable for forming oil-in-water emulsions include, as non-limiting examples, eucalyptus oil (refractive index=1.46), paraffin oil (refractive index=1.480), cedarwood oil (refractive index=1.515), anisole (refractive index=1.518), garlic oil (refractive index=1.57), and bromonaphthalene (refractive index=1.659).

It is also well known in the art that an oil with a particular refractive index can be produced by combining oils of different refractive indexes.

An emulsion is a mixture of two or more liquids that are normally immiscible (i.e. cannot be mixed together). In emulsions, one liquid is dispersed in the form of droplets in the other liquid. Therefore, an emulsion is an ideal sample for both the first and second mixtures of particles as the droplets form a continuum of different particle sizes In the emulsions used to produce FIGS. 1 to 3, the oil is dispersed as droplets within water (i.e. they are "oil-in-water emulsions"). It is preferable to use oil emulsions in embodiments of the invention as the refractive index of oils can be easily controlled.

The histograms of FIGS. 1 to 3 are dual parameter histograms. The histograms show the results recorded by the optical detector used to measure the Small Angle Scatter (SALS) on the x-axis, versus the results recorded by the optical detector used to measure the Large Angle Scatter (LALS) on the y-axis. As can be seen from all of FIGS. 1 to 3, there is a wavelike relationship between the two light scatter signals for both the first and second mixtures. However, the precise form of the histogram produced is highly dependent on the flow cytometer's optics (i.e. the angles at which light is measured by each optical detector).

The data is displayed on the histograms of FIGS. 1 to 3 using a 4.8 logarithmic scale. In embodiments of the invention, the data is displayed on the histogram using a logarithmic scale, preferably a scale of at least 3 log decades, for example a 3, 4.8 or 6 decade logarithmic scale.

The histograms of FIGS. 1 and 2 are single plots. These plots were each produced using the results recorded when a mixture of an oil emulsion and beads was analysed in a cytometer. In each mixture, the oils and beads have the same refractive index to each other. FIGS. 1 and 2 therefore show histograms produced by embodiments of the second mixture of particles of the present invention.

FIG. 1 shows a flow cytometer histogram produced by an oil-in-water emulsion where the oil has a refractive index of 1.59. The circles correspond to latex beads of specific known sizes. The latex beads also have a refractive index of 1.59.

FIG. 2 shows a flow cytometer histogram produced by an oil-in-water emulsion where the oil has a refractive index of 1.42. The rectangles correspond to silica beads of specific known sizes. The silica beads also have a refractive index of 1.42.

The silica and latex beads used to produce FIGS. 1 and 2 have known discrete sizes. In embodiments of the invention, the beads may have any number of known discrete sizes (i.e. sizes $S_1, S_2, S_3 \ldots S_N$).

In some embodiments of the invention, the second mixture may only comprise particles of known discrete size. In such embodiments, the particles of the second mixture do not form a continuum (i.e. a continuous plot) on a flow cytometer histogram, and there should therefore be a sufficient spread of sizes for the a continuous line in the two dimensional histogram data to be inferred.

In other embodiments of the invention, the sizes of the particles in both the first and second mixtures may be generally in a continuum. If the mixtures comprise a continuum of different particle sizes, then the results from the analysis in the cytometer can be used to produce smooth plots on a flow cytometer histogram. Such smooth plots are illustrated by FIGS. 1 to 3. Such smooth plots are preferable as they enable the precise position on the plot of the particles of known size to be more accurately determined An oil emulsion can be used to provide the continuum of particle sizes.

In some embodiments of the invention, each particle of discrete size in the second mixture, for example beads of different sizes are separately analysed in the cytometer in order to determine precisely where this particular size falls on the flow cytometer histogram produced. In alternative embodiments, particles of different discrete sizes are analysed simultaneously in the cytometer.

In embodiments of the invention where the second mixture comprises both beads and an emulsion, the beads and emulsion particles can be analysed simultaneously in the cytometer. In such embodiments, each different size of bead must be present in sufficient concentration for each discrete size population to be visible on the histogram over and above the particles present in the emulsion in order to be able to tell where these specific sizes fall on the histogram.

FIG. 3 shows a histogram produced by the first and second mixture of particles in an embodiment of the invention. In the embodiment of the invention illustrated by FIG. 3, the cytometer is calibrated to a refractive index of 1.404. The first mixture therefore has particles with a refractive index of 1.404. In this embodiment, the particles of the first mixture are oil droplets in an "oil-in-water" emulsion, where the oil has a refractive index of 1.404. The second mixture has particles with a refractive index 1.515.

In embodiments of the invention in which the second mixture comprises an oil emulsion and at least one bead of known size, the oil and beads preferably have the same refractive index to two decimal places. More preferably, the refractive index is the same to three decimal places.

In embodiments of the invention used to produce the histogram of FIG. 3, the range of particle sizes in the second mixture overlaps with the range of particle sizes in the first mixture.

In some embodiments of the invention, the range of particle sizes in the second mixture may encompass the range of particle sizes in the first mixture. Alternatively, the range of particle sizes of the first mixture may encompass the range of particle sizes in the second mixture. In other embodiments, the range of particle sizes in the first mixture may extend at either end of the range of particle sizes in the second mixture (and vice versa).

In the embodiment of the invention used to produce the histogram of FIG. 3, the first mixture produced a first plot (plot 1), and the second mixture produced a second plot (plot 2). Each of these plots can be termed a "light scatter fingerprint", where how the fingerprint varies is dependent on the flow cytometer's optics and the refractive index of the sample being analysed.

In the embodiment of the invention used to produce the histogram of FIG. 3, the results from the first and second mixtures were recorded simultaneously. The first and second plots are therefore shown on a single histogram. However, in alternative embodiments, the results from the first and second mixtures can be recorded at different times, producing separate flow cytometer histograms for each plot.

In embodiments of the invention in which the first and second mixtures both comprise oil emulsions, in order to record the results from the first and second mixtures simultaneously, the two oils used to form the emulsions should be immiscible in each other.

In the embodiment of the invention used to produce FIG. 3, the position of particles of a particular size and refractive index 1.515 on plot 2 is used to infer where particles of the same size and refractive index 1.404 lie on plot 1. For example, the position of a particle of size A with refractive index 1.515 has been labeled on plot 2, and this information has been used to determine where a particle of size A with refractive index 1.404 falls on plot 1.

The Mie solution to Maxwell's equations predicts the relationship between the intensity of scattered radiation and particle size. It is therefore possible to determine the size of a particle from its position on the flow cytometer histogram.

As stated in Hendrik C van de Hulst's "Light Scattering by Small Particles", Dover Publications, 1957, the angular variation of the light scattering is independent of the refractive index of the particles. Therefore, if there are two flow cytometer histograms (for example, plots 1 and 2 of FIG. 3), each produced by a different mixture of particles, where the particles of each of these mixtures have a different refractive index, particles of the same size will fall at the same positions on the two light scatter histograms relative to points of inflection, such as peaks and troughs, on the graphs.

Referring to FIG. 3, particles of size A with a refractive index of 1.404 are found to fall on the first trough of plot 1, and so particles of size A with a refractive index of 1.515 must fall on the first trough of plot 2.

Therefore, the position of particles of known size on plot 2 can be used to determine where the same sized particle sizes fall on plot 1. As plot 1 comprises particles with the refractive index that the cytometer is being calibrated to, this method calibrates the cytometer to the desired refractive index.

When a sample is then analysed in the cytometer, the results produced can be compared to plot 1 in order to determine the particle size of the sample. If the sample has a refractive index that is substantially the same as or similar to the refractive index of calibration, then this method will be able to accurately determine the particle size of the sample.

As a further illustrative example, in an embodiment comprising a first mixture with particles of refractive index 1.38, and a second mixture with particles of refractive index 1.59, if 1 µm polystyrene beads (i.e. beads with a diameter of 1 µm) with a refractive index of 1.59 fall on the third trough of the plot produced by the second mixture, then 1 µm particles with a refractive index of 1.38 would fall on the third trough of the plot produced by the first mixture.

The present invention therefore discloses a method and system for calibrating the cytometer so that the size of particles in a sample can be accurately determined (i.e. a method of "size calibration").

Alternatively, if the size of the particles in a sample to be analysed in a cytometer is known, the method and system of the present invention could instead be used to infer the refractive index of particles in a sample. For example, if a flow cytometer histogram has two plots, one produced by an oil emulsion with an oil with a refractive index of 1.59, the other with by an oil emulsion with an oil with a refractive index of 1.38, and a 1 µm particle falls on the part of the 1.59 plot known to be produced by 1 µm sized particles, then it can be deduced that the 1 µm particle has a refractive index of 1.59.

In alternative embodiments of the invention (not shown in the figures), the cytometer is calibrated to a particular refractive index using fluorescence.

This calibration method requires the particles of the first and second mixtures to comprise a specific number of fluorescent molecules per unit volume. An emulsion formed with an oil to which fluorescent molecules have bound is, therefore, suitable for use in these embodiments of the calibration method.

A flow cytometer's fluorescence signal is proportional to the number of fluorescent molecules present in a particle. The fluorescence scale can be calibrated by analysing commercially available particles containing a known number of fluorescent molecules per particle. Once the fluorescence scale has been calibrated, the number of fluorescent molecules per particle can be determined for samples analysed in the cytometer. In addition, if a histogram is produced using the fluorescence readings obtained when a sample is analysed in the cytometer, the relationship between number of fluorescent molecules and position on the histogram is then known.

If the absolute number of fluorescent molecules per volume of particle material is known, this means that a calibrated fluorescence scale on the flow cytometer tells you the particle size.

However, in embodiments of the invention, the absolute number of fluorescent molecules per unit volume of the particles of the first and second mixtures is not known. Instead, the relationship between the amount of fluorescence in same sized particles of the first and second mixtures is used to calibrate the cytometer.

For example, knowing the relationship between the number of fluorescent molecules in the oils used to form the first and second mixtures allows the relationship between the oil droplets' sizes to be inferred, and thus allows creation of a calibrated scale on the light scatter histogram for a particular refractive index.

For example, if the first and second mixtures comprise oil-in-water emulsions made with oils containing equal quantities of a fluorescent molecule per unit volume, droplets of these two oils of equal size will emit the same strength of fluorescence when analysed in a flow cytometer. In other words, particles of the first and second mixtures with equal fluorescence will be particles of equal size.

The relationship between size and fluorescence per unit volume of particles in a mixture can be determined using at least one particle of a specific known size (for example, a polystyrene, silica or latex bead) which has the same refractive index as the other fluorescent particles in that mixture.

As particles of known discrete size that have the refractive index of calibration are often difficult to find, in embodiments of the invention, two different mixtures of particles are used to calibrate the cytometer to the desired refractive index. The particles of the first mixture have the refractive index of calibration, and the particles of the second mixture have any other refractive index for which it is possible to find at least one particle of known size. The at least one particle of known size therefore forms part of the second mixture.

In embodiments of the invention, both of the first and second mixtures are analysed in a cytometer, and a flow cytometer histogram of a light scatter signal (for example, the small-angle scatter or the large-angle scatter) versus the fluorescence signal (with a count of the number of particles as a density gradient) is produced using the results. This flow cytometer histogram comprises two plots: one from the first mixture and one from the second.

The particle of known size is also separately analysed in the cytometer. This enables its position to be marked on the plot from the second mixture on the flow cytometer histogram. As the flow cytometer histogram has the fluorescence signal on one of its axes, the amount of fluorescence produced by this particular particle size of the second mixture can be determined. Then, if the fluorescence scale has been calibrated, the number of fluorescent molecules needed to produce that amount of fluorescence is known, and the number of fluorescent molecules per unit volume can be determined. Then, if the relationship between the amount of fluorescence of same sized particles of the first and second mixtures is known, this can be used to determine the number of fluorescent molecules per unit volume of the first mixture, and particle size information can then be marked on the plot from the first mixture. This method therefore allows the cytometer to be calibrated to the refractive index of the first mixture.

Similarly, if the flow cytometer's fluorescence optics are calibrated for a particular fluorochrome, an oil emulsion with known amount of that fluorochrome per unit volume of oil could be used to calibrate the light scatter optics for particles of the same refractive index as the oil.

Figure 4:
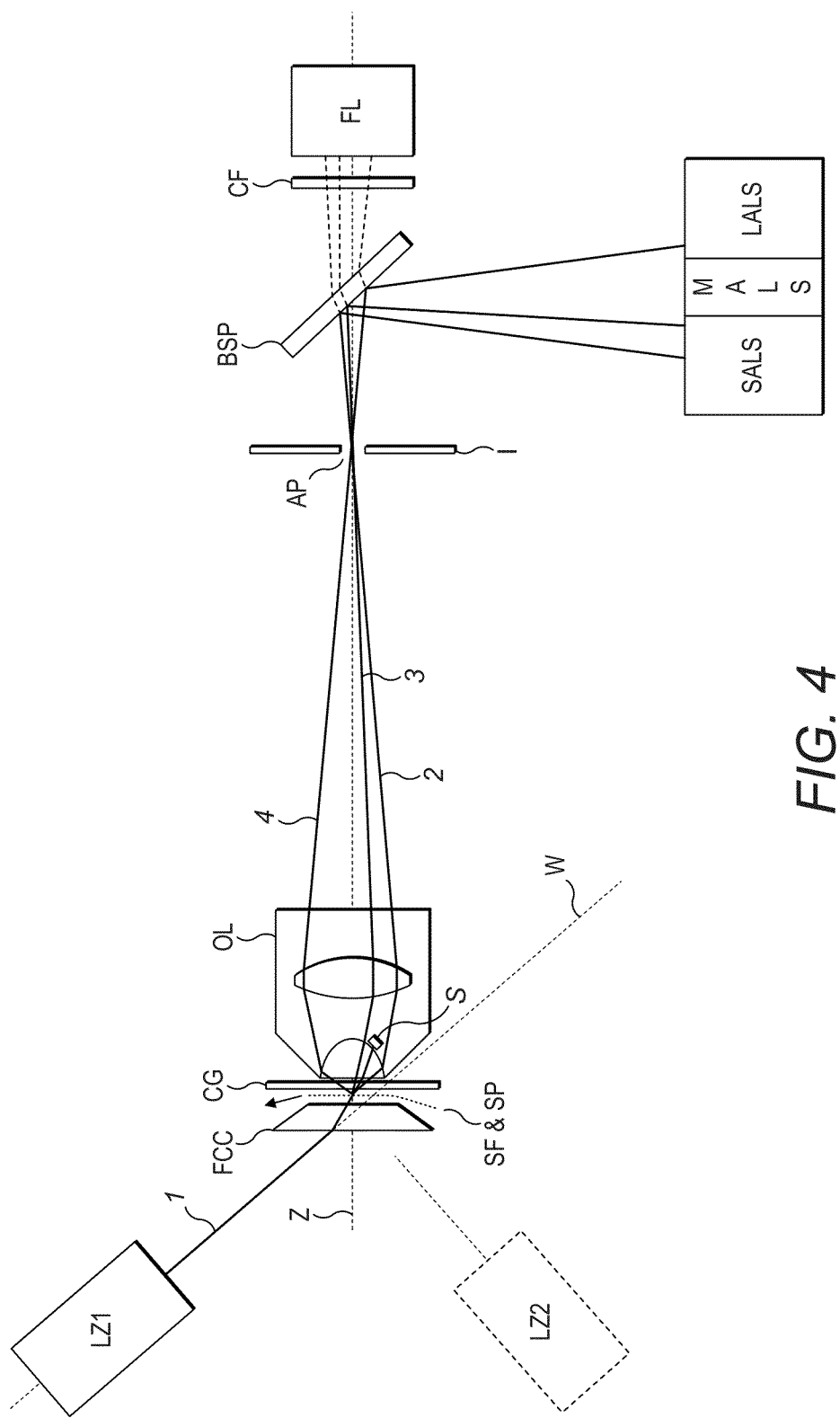
FIG. 4 is a schematic representation of an optical system of a flow cytometer.

FIG. 4 shows a schematic representation of an optical system of a flow cytometer. In the figure, a sheath fluid (SF) and sample particles (SP) are shown flowing upwards into a flow channel between a flow cell crystal (FCC) and a coverglass (CG). The sheath fluid is used to hydro-dynamically focus the sample particles into a narrow stream. A laser (LZ1) and beam shaping optics (not shown) produce a beam of radiation (1) along an optical axis (W), incident upon a flow cell crystal (FCC) at angle. A microscope lens (OL) is used to collect light from the flow cell channel through the coverglass (CG).

The directly transmitted laser beam is prevented from travelling to a series of optical detectors (fluorescence detector (FL), SALS detector, MALS detector, LALS detector), by a beam stop (S). Scattered rays (2, 3 and 4) pass by the beam stop and travel on to image plane (I), conjugate with the sample stream. At the image plane an aperture (AP) spatially filters light from the flow cell to exclude background scattered light.

A dichroic beam splitter (BSP) may be located after the aperture (AP) to allow fluoresced light (of longer wavelength than the illumination light) to pass on to one or more fluorescence detectors. Additional dichroic beam splitters and detectors may be incorporated to detect several types of fluorescent molecules. The beam splitter (BSP)

reflects scattered laser light towards one or more light scatter detectors (SALS, MALS and LALS).

In some embodiments, additional colour filters (CF) may be placed in front of the fluorescence detector(s) to improve signal to noise ratios. Similarly, polarisation filters may be placed in front of the light scatter detectors to measure polarisation differences between light from different particles.

The invention allows the use of additional light (radiation) sources, typically of a different wavelength. For example, a second laser source (LZ2) may be positioned as a mirror image about the collection optical axis (Z) of the first light source (LZ1).

The invention claimed is:

1. A method of calibrating a flow cytometer to a refractive index X, the method comprising:
    analyzing a first mixture of particles in the cytometer and recording the results produced, wherein the first mixture comprises particles having refractive index X, wherein the particles of refractive index X have a plurality of different sizes;
    analyzing a second mixture of particles in the cytometer and recording the results produced, wherein the second mixture comprises particles having refractive index Y, wherein refractive index Y does not equal refractive index X, and wherein the particles of refractive index Y have a plurality of different sizes, wherein there is at least a partial overlap between the particle sizes in the first and second mixtures, and wherein the size of at least one particle of the second mixture is known; and using the results produced by the first and second mixture to calibrate the cytometer to refractive index X.

2. A method of calibrating a flow cytometer as claimed in claim 1, wherein the second mixture comprises particles of refractive index Y that have at least a plurality of known discrete sizes.

3. A method of calibrating a flow cytometer as claimed in claim 2, wherein the particles of the second mixture having known discrete sizes comprise at least one of beads of plastic, latex, or silica.

4. A method of calibrating a flow cytometer as claimed in claim 1, wherein at least some of the particles of the first and second mixtures with refractive indexes X and Y comprise one or more fluorescent molecules, wherein the relationship between the fluorescence of particles of the first and second mixtures is known.

5. A method of calibrating a flow cytometer as claimed in claim 1, wherein the first mixture comprises an emulsion and particles of the first mixture comprise droplets of a liquid of the emulsion with refractive index X.

6. A method of calibrating a flow cytometer as claimed in claim 5, wherein the droplets are formed from oils.

7. A method of calibrating a flow cytometer as claimed in claim 5, wherein the emulsions comprise water.

8. A method of calibrating a flow cytometer as claimed in claim 1, wherein the second mixture comprises an emulsion and the particles of the second mixture comprise droplets of a liquid of the emulsion with refractive index Y.

9. A method of calibrating a flow cytometer as claimed in claim 8, wherein the droplets are formed from oils.

10. A method of calibrating a flow cytometer as claimed in claim 8, wherein the emulsions comprise water.

11. A method of calibrating a flow cytometer as claimed in claim 1, wherein the size of the particles in the first and second mixtures lie in a range between 50 nm and 50 µm.

12. A method of calibrating a flow cytometer as claimed in claim 1, wherein refractive index X lies in the range 1.34 to 1.58.

13. A method of calibrating a flow cytometer as claimed in claim 1, wherein the results are recorded from the first or second mixtures independently.

14. A method of calibrating a flow cytometer as claimed in claim 13, wherein the first and second flow cytometer histograms are one-dimensional histograms of a count of the number of particles versus the strength of the signal produced by the particle in the flow cytometer.

15. A method of calibrating a flow cytometer as claimed in claim 13, wherein the first and second flow cytometer histograms are two-dimensional histograms of two light scatter angle ranges with a count of the number of particles as a density gradient.

16. A method of calibrating a flow cytometer as claimed in claim 13, wherein the first and second flow cytometer histograms are two-dimensional histograms of a light scatter signal and a fluorescence signal with a count of the number of particles as a density gradient.

17. A method of calibrating a flow cytometer as claimed in claim 1, wherein the results are recorded from the first and second mixtures simultaneously.

18. A method of calibrating a flow cytometer as claimed in claim 1, comprising:

using the results produced by the first mixture of particles to produce a first plot on a first flow cytometer histogram;

using the results produced by the second mixture of particles to produce a second plot on a second flow cytometer histogram;

recording where the plurality of known particle sizes of the second mixture lie on the second plot; and using the position of the known particle sizes on the second plot to determine where the particles of the same size lie on the first plot.

19. A method of calibrating a flow cytometer as claimed in claim 18, wherein the first and second flow cytometer histograms are two-dimensional histograms of the small-angle scatter versus the large-angle scatter.

20. A system for calibrating a flow cytometer to a refractive index X, the system comprising:

a first mixture of particles, wherein the first mixture of particles is configured to be analyzed in the cytometer and results produced are recorded, wherein the first mixture comprises particles of refractive index X, wherein the particles of refractive index X have a plurality of different sizes; and a second mixture of particles, wherein the second mixture of particles is configured to be analyzed in the cytometer and results produced are recorded, wherein the second mixture comprises particles of refractive index Y, wherein refractive index Y does not equal refractive index X, and wherein the particles of refractive index Y have a plurality of different sizes, wherein there is at least a partial overlap between the particle sizes in the first and second mixtures, and wherein the size of at least one particle of the second mixture is known, wherein the results produced by the first and second mixture are configured to calibrate the cytometer to refractive index X.

* * * * *